United States Patent [19]

Nimrod et al.

[11] Patent Number: 4,784,991

[45] Date of Patent: Nov. 15, 1988

[54] HEAVY METAL SALTS OF HYALURONIC ACID AND THEIR USE AS ANTIMICROBIAL AGENTS

[75] Inventors: Abraham Nimrod; Benjamin Greenman, both of Rehovot, Israel

[73] Assignee: Bio-Technology General Corp., New York, N.Y.

[21] Appl. No.: 23,666

[22] Filed: Mar. 9, 1987

Related U.S. Application Data

[63] Continuation-in-part of Ser. No. 840,419, Mar. 14, 1986.

[51] Int. Cl.$^4$ .................... A61K 7/32; A01N 63/02
[52] U.S. Cl. .................................. 514/62; 514/21; 514/495; 514/500; 424/65; 424/95
[58] Field of Search ............... 424/1.1, 63, 64, 70, 424/78, 81, 95, 19-22; 514/15, 54, 495, 781, 800, 844, 886, 887, 912, 914, 8.62, 500; 524/27, 29; 525/54.2; 433/177; 536/4.1; 623/11, 16; 604/890-897

[56] References Cited

U.S. PATENT DOCUMENTS

| | | | |
|---|---|---|---|
| 4,172,128 | 10/1979 | Thiele et al. | 424/95 |
| 4,211,769 | 7/1980 | Okado et al. | 514/800 |
| 4,487,865 | 12/1984 | Balazs et al. | 525/54.2 |
| 4,605,691 | 8/1986 | Balazs et al. | 524/27 |

OTHER PUBLICATIONS

"Cu$^{+2}$ Hyaluronic Acid Complex:Spectrophotometric Detection", Figueroa et al, *Biochemical and Biophysical Research Communications* 74(2), 460-465, 1975.
"Hyaluronic Acid Conformations Observed for Various Salt Forms in the Crystaline Phase", Atkins et al., *Connective Tissue Research* 62(2), 116, (1978).

Primary Examiner—Barry S. Richman
Assistant Examiner—T. J. Wallen
Attorney, Agent, or Firm—John P. White

[57] ABSTRACT

Heavy metal salts of hyaluronic acid have been prepared. In particular, this invention is directed to silver, gold, cerium and tungsten salts of hyaluronic acid. These heavy metal salts of hyaluronic acid are useful as antimicrobial agents. Gold hyaluronate may also be used to treat arthritis.

This invention also concerns methods of making the silver salt of hyaluronic acid as well as compositions containing silver hyaluronate or gold hyaluronate.

The invention also concerns composition containing heavy metal salts having radioactively labelled hyaluronate moieties.

2 Claims, 1 Drawing Sheet

SLOW RELEASE OF Ag$^+$ FROM AgHA

SLOW RELEASE OF $Ag^+$ FROM AgHA

HEAVY METAL SALTS OF HYALURONIC ACID AND THEIR USE AS ANTIMICROBIAL AGENTS

This application is a continuation-in-part of Ser. No. 840,419, filed Mar. 14, 1986, the contents of which are hereby incorporated by reference into the present applicatilon.

BACKGROUND OF THE INVENTION

Throughout this application various publications are referenced by arabic numerals with parentheses. Full citations for these references may be found at the end of the specification immediately preceding the claims. The disclosures of these publications in their entireties are hereby incorporated by reference into this application in order to more fully describe the state of art as known to those skilled therein as of the date of the invention described and claimed herein.

This invention concerns the heavy metal salts of hyaluronic acid.

Hyaluronic acid is present in various connective tissues of animals, such as skin and cartilage. Some organs are specifically rich in hyaluronic acid, such as the umbilical cord, synovial fluid, the vitreous humor and rooster combs. In addition, hyaluronic acid is produced by various microorganisms, such as streptococci Type A and C.

In skin and cartilage, the role of hyaluronic acid is to bind water and retain the tonicity and elasticity of the tissue. In joint fluids, the viscous hyaluronic acid solution serves as a lubricant to provide protective environment to the cells. A solution of ultrapure hyaluronic acid from rooster combs has been in use for several years as a supportive medium in ophthalmic surgery, see U.S. Pat. No. 4,141,973 of E. A. Balazs (1979). A similar preparation has been shown to be beneficial in the treatment of inflamed knee joints of race horses. Another use of hyaluronic acid results from its highly hydrophilic nature, making it an ideal constituent of moisturization lotions for cosmetic use, U.S. Pat. No. 4,303,676 of E. Balazs (1981).

Hyaluronic acid has been isolated from the various biological sources, as described above, including microbial broth. The isolation and characterization of hyaluronic acid has been described by Meyer et al., J. Biol. Chem. 107,629 (1934); J. Biol. Chem. 114,689 (1936), and has recently been reviewed in Methods in Enzymol. 28, 73 (1972). The structure of hyaluronic acid was elucidated by Weissman et al., J. Am. Chem. Soc. 76, 1753 (1954) and Meyer, Fed. Proc. 17, 1075 (1958). Other publications such as, U.S. Pat. No. 4,141,973, Feb. 27, 1979 by E. A. Balazs, concerned the production and purification of hyaluronic acid from the sources such as animal connective tissue.

Radioactively labelled hyaluronic acid and sodium salt thereof has been produced by growing streptococcus in fermentation broth containing radioactively labelled glucose.

Numerous silver compounds having a wide range of uses are known. These include silver acetate and silver chlorate which may be used as oxidizing agents; silver bromide and silver oxalate which are used in photography; silver difluoride for use in the flourination of hydrocarbons; silver chloride and silver cyanide for use in silver plating; and silver chromate (VI) and silver oxide which may be employed as catalysts, to name just a few.

The silver ion has also been shown to be an effective antimicrobial agent. It is not associated with significant side effects, is not an allergen, and is only rarely associated with the induction of resistant strains of bacteria. Many silver salts are useful as topical anti-infectives or as antiseptics. These include: silver fluoride, silver iodide, silver lactate, mild silver protein and silver nitrate. Silver lactate and silver nitrate may also be employed as astringents and silver picrate and silver sulfadiazine may be used as antimicrobial or antibacterial agents.

It is believed that silver compounds produce their antimicrobial effects by the time-dependent release of silver ions and their effectiveness is directly related to the constant presence of the free ions in the tissues. The use of simple silver salts, such as silver nitrate, as an antibacterial agent has been limited by the requirement of frequent applications to achieve effective concentrations of the silver ions (10-20 ug/ml).

Although the use of silver sulfadiazine, a more complex silver compound, results in a more sustained release of the silver metal ions, the use of both silver nitrate and silver sulfadiazine is often accompanied by adverse side-effects due to the anion part of the salts, namely nitrate and sulfadiazine. For example, sulfadiazine has such side effects as leucopenia and immunosuppression activity. Other silver preparations, such as foils and silver nylon, have recently been offered for use, but their release of silver ions is limited and do not result in high enough concentrations. The use of salts is important because complexes may not provide the steady release ions needed to obtain optimal concentrations.

Thus, the need for a silver compound providing sustained release of the silver metal ion, but having no adverse side effects is apparent.

Rheumatoid arthritis is characterized by severe inflammation of the joints which is followed by the appearance of degraded hyaluronic acid in the joint fluid. In severe cases, anti-inflammatory agents such as corticosteroids and gold salts, e.g. gold sodium thiomalate or gold sodium thiosulfate are administered intra-articularly. However these agents are active for only a short duration, and there is a need to sustain their action. Thus, the invention of an anti-inflammatory agent having sustained action would meet a long felt need and be a significant advance in the anti-inflammatory art.

The present invention is directed to heavy metal salts of hyaluronic acid, including silver hyaluronate, gold hyaluronate, cerium hyaluronate, and tungsten hyaluronate.

The invention is also directed to methods of inhibiting microbial growth utilizing these heavy metal salts.

The present invention concerns methods of producing silver hyaluronate, compositions containing silver hyaluronate, and the treatment of wounds, burns and infections, especially soft-tissue infections and gonoccocal ophthalmalogical infections, with silver hyaluronate.

The invention further concerns a method for treating keratitis with silver hyaluronate and optionally in conjunction with antibiotics.

The invention further provides for incorporation of heavy metal hyaluronate salts into deodorants and into cosmetic creams, lotions and sprays.

The invention also concerns treating arthritis and joint inflammation with gold hyaluronate.

Finally, this invention is directed to compositions containing radioactively labelled heavy metal salts e.g.

$^{14}$C AgHA, which compositions may be used for diagonstic purposes.

SUMMARY OF THE INVENTION

The invention concerns heavy metal salts of hyaluronic acid, in particular, silver hyaluronate, gold hyaluronate cerium hyaluronate, and tungsten hyaluronate.

The invention also concerns methods of making the silver hyaluronate by mixing aqueous sodium hyaluronate (NaHA) solution with a molar excess of aqueous silver nitrate (AgNO$_3$) solution to form aqueous silver hyaluronate (AgHA) solution, precipitating the silver hyaluronate from the solution and recovering the precipitated silver hyaluronate.

These heavy metal salts of hyaluronic acid may be incorporated into compositions, such as pharmaceutical compositions containing an effective amount of the heavy metal salt, e.g., silver hyaluronate or gold hyaluronate, and a pharmaceutically acceptable carrier.

These heavy metal salts of hyaluronic acid are useful as antimicrobial agents. In particular, microbial growth may be inhibited by contacting the microbes with an effective amount of silver hyaluronate. Silver hyaluronate may also be used to inhibit microbial growth in infections, by topically applying an effective amount of the silver hyaluronate to the infection.

The heavy metal salts are also useful when incorporated into deodorants and may also be used in cosmetic creams, lotions and sprays.

Gold hyaluronate may be used to treat arthritis and joint inflammation by administering an effective amount of the gold hyaluronate intra-articularly to the afflicted subject.

This invention also concerns compositions containing heavy metal salts of radioactively labelled hyaluronic acid.

BRIEF DESCRIPTION OF THE FIGURES

To test the Ag ion release propeties of AgHA, a sample containing 1800 ug of Ag ion was dialyzed against distilled water at room temperature. At points indicated in FIG. 1, the dialysis bag containing AgHA was transferred to 500 ml fresh distilled water. At each point a sample of the water was removed and the concentration of Ag ions determined by atomic absorption. The results in FIG. 1 show that Ag ions are released in a slow manner, as 70% of the Ag ion concentration was retained in the dialysis bag after 48 h.

DETAILED DESCRIPTION OF THE INVENTION

This invention concerns heavy metal salts of hyaluronic acid. More particularly, the salts encompassed by this invention include the silver, gold, cerium, and tungsten salts of hyaluronic acid.

The invention also concerns methods of making the silver salt of hyaluronic acid by mixing aqueous sodium hyaluronate (NaHA) solution with a molar excess of aqueous silver nitrate (AgNO$_3$) solution to form aqueous silver hyaluronate (AgHA) solution, precipitating the silver hyaluronate from the solution and recovering the precipitated silver hyaluronate. The silver hyaluronate precipitate may be recovered by separating the silver hyaluronate precipitate from the aqueous silver hyaluronate solution, e.g., by centrifugation, washing the separated precipitate with ethanol and drying the washed precipitate over nitrogen.

Preferably, the silver hyaluronate is prepared in the absence of light and the aqueous sodium hyaluronate and aqueous silver nitrate mixture is shaken for a sufficient period of time, ordinarily several hours, to form aqueous silver hyaluronate solution. The aqueous silver hyaluronate solution is then treated to effect precipitation of the silver hyaluronate which may be recovered by rinsing the silver hyaluronate precipitate with ethanol, drying the rinsed precipitate with nitrogen and further drying the nitrogen-dried precipitate by high vacuum drying.

The other heavy metal salts of hyaluronic acid may be prepared by methods analogous to the preparation of silver hyaluronate.

These heavy metal salts of hyaluronic acid may be combined with carriers to form compositions. The carrier or carriers may be any suitable carrier known to those of ordinary skill in the art. These compositions may be pharmaceutical compositions containing an effective amount of the heavy metal salt of hyaluronic acid, for example, silver hyaluronate, or gold hyaluronate and a pharmaceutically acceptable carrier.

The heavy metal salts of hyaluronic acid and compositions d containing same are useful as antimicrobial agents. In particular, microbial growth may be inhibited by contacting the microbes with an effective amount of silver hyaluronate. Silver hyaluronate may also be used for treating burns, wounds, soft tissue infections, for example, gonoccocal opthalmalogical infections or sepsis by topically applying an effective amount of the silver hyaluronate to the site of the burn, wound, soft tissue infection or infection from which the sepsis stems. Silver hyaluronate compositions are also used for treating keratitis infections.

In another aspect of the invention, heavy metal hyaluronate salts are incorporated into deodorants, cosmetic creams, lotions and sprays.

Gold hyaluronate may also be used for treating arthritis, rheumatoid arthritis, and joint inflammation in a subject by administering an effective amount of the gold hyaluronate intra-articularly to the subject.

This invention also concerns compositions containing the radioactively labelled heavy metal salts of hyaluronic acid. These include salts wherein the hyaluronate moiety is radioactively labelled, as well as salts wherein the heavy metal is in isotope form. Preferably, the radioactively labelled heavy metal salt is a heavy metal salt of radioactively labelled hyaluronic acid. More preferably, the hyaluronate moiety is radioactively labelled with $^{14}$C. Preferably the heavy metal is silver. Most preferably the radioactively labelled heavy metal salt is $^{14}$C radioactively labelled silver hyaluronate. These radioactively labelled heavy metal salts and compositions containing them may be used for diagnostic purposes.

As used throughout this application the term "heavy metal" includes any metal in Period 5, 6, or 7 or the 4f (Lanthanide) or 5f (Actinide) series of the Periodic Table.

Hyaluronic acid (HA) is a major constituent of connective tissue, body fluids and skin, and hence is absolutely non-immunogenic. Due to their large size (M.W. $1.5 \times 10^6$ Daltons), HA salts form viscous solutions, and after injection into the tissues the polysaccharide diffuses extremely slowly from the injection site.

Naturally occuring hyaluronic acid is a glycosaminoglycan consisting of a linear polymer of molecular weight of 50,000–13,000,000 daltons. It is a polysaccharide made of a repeating units of glucuronic acid and N-acetyl-glucosamine, bound by alternating 1-3 and 1-4 bonds.

As employed throughout this application the term "hyaluronic acid" includes substantially pure naturally occurring or synthetic hyaluronic acid, hyaluronic acid derivatives, hyaluronic acid cross-linked with itself, and hyaluronic acid cross linked with other substances such as collagen. See WO No. 86/00079 and WO No. 86/00912.

EXPERIMENTAL DETAILS

EXAMPLE 1

PREPARATION OF SILVER HYALURONATE (AGHA)

Silver hyaluronate has been prepared as follows:

A. One volume of sodium hyaluronate solution in water (0.5% of purified bacterially-derived sodium hyaluronate, M.W. $2.7 \times 10^6$ daltons) was mixed with 1 volume of 0.5M $AgNO_3$ in water. Two volumes of ethanol were then added, and the precipitated silver salt was centrifuged, washed with ethanol and dried over nitrogen. The silver content of this hyaluronate salt was found by atomic absorption to be 20% w/w, i.e., corresponding to approximately 92% substitution of the carboxylic ions.

This preparation was found to effectively kill Staphylococci, Pseudomonas, Candida Albicans and Candida Tropicans when applied as a 0.1% solution (1:1, v/v) to cultures containing $10^6$ microorganisms per ml.

B. Preliminary studies have indicated that removal of traces of chloride ions is essential for obtaining a relatively stable, pure and clear AgHA product. This has been achieved by ethanolic precipitation of sodium HA from a sodium nitrate solution. The procedure for the production of AgHA, starting with 1 gram of pure clinical grade sodium hyaluronate, is as follows:

1. Pharmaceutical grade NaHA (1 gram) is dissolved in 200 ml of 0.5M $NaNO_3$.
2. 300 ml of ethanol is added, and the precipitated NaHA collected and washed thoroughly with 96% ethanol.
3. The precipitate is redissolved in 200 ml of double distilled water.
4. 200 ml of 0.5M $AgNO_3$ is added in the dark and the mixture shaken for several hours. All subsequent operations are performed in relative darkness.
5. Ethanol (600 ml) is added, and the precipitated AgHA is rinsed with 96% ethanol, dried with nitrogen, then followed by high vacuum drying.

Portions of the final material are taken and redissolved in sterile, double-distilled water to give a working solution. A 1% solution gives a viscous, clear liquid with a brownish color.

EXAMPLE 2

PROPERTIES OF AGHA

Several batches of this material have been prepared.
Silver Content:
Analysis of the silver content, as determined by atomic absorption, was 82 grams per mole, which is 76% of the theoretical stoichiometrical value, while the concentration of residual sodium ions was 0.5% of the theoretical value.
Stability Studies:
Some preliminary observations of the stability of the 1% AgHA solutions have been made. Storage in the dark under refrigeration had no effect on the appearance of the material: no changes in viscosity or darkening of the clear solution have developed during 3-4 months. However, exposure of the solution to room temperature and light resulted in gradual browning, development of turbidity and a drop in viscosity within a week to two weeks.

Molecular Weight:
The various batches of AgHA were prepared from NaHA of M.W. of $3-3.5 \times 10^6$. In order to measure the M.W. of AgHA, the material had to be converted to the Na form. This was done by ethanol precipitation from a concentrated (1M) solution of $NaNO_3$. The M.W., as deduced from limiting viscosity measurements with these precipitates, was found to be $1.7-2 \times 10^6$ daltons immediately after preparation of the AgHA solutions. On the shelf, at room temperature and lighting, the M.W. dropped to:

$1.27 \times 10^6$ daltons after 7 days;
$0.96 \times 10^6$ daltons after 29 days.

EXAMPLE 3

SLOW RELEASE OF AG IONS FROM AGHA

Figure 1:
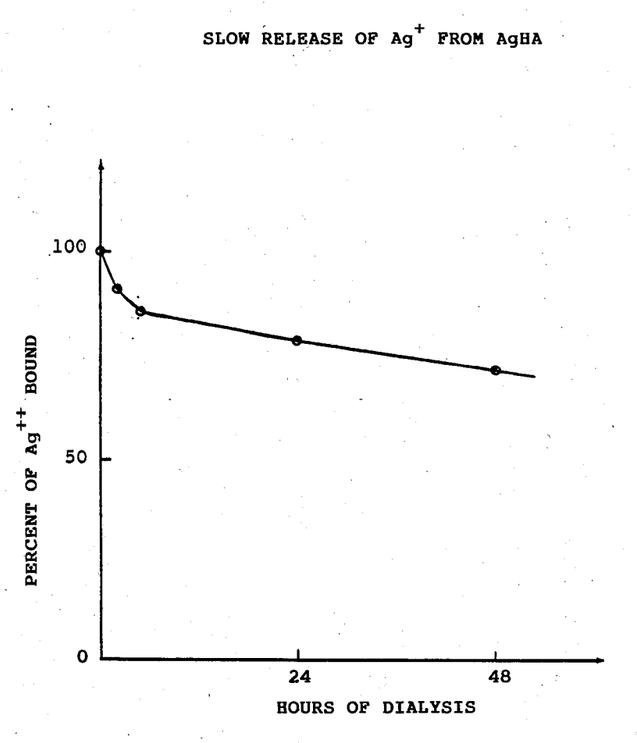
FIG. 1: Slow Release of Ag Ions from AgHA

Slow release of Ag ions is mandatory for a long-lasting effect of the antimicrobial in the form of Ag complex. To test the Ag ion release properties of AgHA, a sample containing 1800 ug of Ag ion was dialyzed against distilled water at room temperature. At points indicated in FIG. 1, the dialysis bag containing AgHA was transferred to 500 ml fresh distilled water. At each point a sample of the water was removed and the concentration of Ag ions determined by atomic absorption. The results in FIG. 1 show that Ag ions are released in a slow manner, as 70% of the Ag ion concentration was retained in the dialysis bag after 48 h. The calculated dissociation constant of AgHA, assuming 100% dissociation of free HA, is $6.7 \times 10^{-5}$M.

EXAMPLE 4

EFFICACY OF AGHA

A. Minimal Inhibitory Concentration. Minimal inhibitory concentration was tested on eight species of bacteria isolated from hospitalized patients. The eight species are *E. coli;* Seratia; Pseudomonas; Proteus; *K. pneumoniae;* Acinobacter; *C. albicans;* and *M. morgani.*

AgHA was diluted in 0.25% NaHA to yield final concentration in growth media of 100, 50, 40, 20, 10 ug/ml of silver ion equivalent. The growth media was L broth containing no NaCl and supplemented with NaHA to a final concentration of 0.25%. The latter NaHA concentration was chosen as standard concentration for growth in liquid media because some bacteria did not grow as well at concentration of 0.5% (Table 1). Concentrations of 0.5% NaHA and above slowed the growth rate. This is attributed to the high viscosity of the media which apparently reduced oxygen solubility.

2 ml cultures were inoculated with approximately $10^5$ cells and grown on a rotary shaker at 37° C. for 72 h. After 24, 48 and 72 hours, cultures were scored for growth. A slight turbidity observed in test tubes was scored as growth and marked in tables with the notation + (plus) (Table 2).

To compare the efficacy of AgHA to that of Ag-Sulfadiazine, L broth media containing concentrations of silver ions identical to those used for AgHA were prepared by serial dilutions. Growth and scoring methodology were the same as described previously (Table 3). For a control experiment, L broth containing silver nitrate at identical concentrations of silver ions to those used for AgHA and Ag-Sulfadiazine were used (Table 4). The results of these experiments are presented in Table 3 and Table 4. The data obtained indicate that except for *C. abicans* and *K. pneumoniae,* all other clinical isolates were inhibited by a concentration of 20 ug/ml silver ions. A concentration of about 40 ug/ml was needed to inhibit growth of *C. Albicans* and *K. Pneumoniae.* It is clear that AgHA inhibits microbial growth.

B. Double Agar-Layer Test. Ag compounds are most commonly used as ointments. Ag ions have to be released and reach the target by diffusion. The methodology used to test this aspect of AgHA was adopted from Dettch et al. (2) and modified by using petri plates. AgHA and Ag-Sulfadiazine were mixed with agar separately to yield a calculated concentration of 40 ug/ml silver ions. A layer of 2.2 mm silver containing agar was first poured and after solidification a layer of L-agar of 2.2 or 2.0 mm was poured on top. The plates were aged for 24, 48, 72, and 96 h prior to use. Cultures of bacteria were grown overnight and diluted in L broth media to yield about $10^5$–$10^6$ cells. 0.1 ml of diluted cultures were applied to each plate to yield a final concentration of $10^4$–$10^5$ cells per plate. No Ag ions were used in the control experiments when determining total viable cells per plate. Table 5 and Table 6 show the results obtained for AgHA and Ag-Sulfadiazine. The results are shown in fraction form as the number of cells which grew on the silver ion plates (numerator) over the number of cells which grew on the control plates containing no silver (denominator). The fraction is also expressed as a percent. In Table 5 the results correspond to the experiment where the upper layer of L agar was 2.0 mm. Except for *C. albicans,* more than 99% of the population of the different species were fully inhibited. The surviving fraction was higher in the experiment shown in Table 6 than that shown in Table 5. This is attributed to the fact that the upper L-agar layer was 2.2 mm. Dettch found that each increase of 2 mm in height of the upper agar layer increased survival number tenfold. The increase of 0.2 mm in height of L-agar in our experiments is in agreement with the above finding, as the number of survivals did not exceed 2–3%. No significant difference is observed between plates aged for 24–96 h, indicating that by 24 h the minimum concentration of silver ions has reached the L-agar surface.

TABLE 1

Effect of Hyaluronate on Bacterial Growth Rates Generation Time in Different Concentrations of Hyaluronic Acid Sodium Salt (minutes)

| Strain | 0 | 0.05% | 0.10% | 0.25% | 0.50% |
| --- | --- | --- | --- | --- | --- |
| E. coli | 30 | 28 | 33 | 30 | 50 |
| Pseudomonas | 45 | 48 | 48 | 60 | 140 |
| Seratia | 29 | 30 | 31 | 33 | 30 |

TABLE 2

Minimal Inhibitory Concentration in Liquid Medium Ag—HA

| Conc. of Ag+ | 100 ug/mlAg+ Hour | | | 50 ug/ml Hour | | | 40 ug/ml Hour | | | 20 ug/ml Hour | | | 10 ug/ml Hour | | |
| --- | --- | --- | --- | --- | --- | --- | --- | --- | --- | --- | --- | --- | --- | --- | --- |
| Strain | 24 | 48 | 72 | 24 | 48 | 72 | 24 | 48 | 72 | 24 | 48 | 72 | 24 | 48 | 72 |
| E. coli | − | − | − | − | − | − | − | − | − | − | − | − | − | + | + |
| Seratia | − | − | − | − | − | − | − | − | − | − | − | − | + | + | + |
| Pseudomonas | − | − | − | − | − | − | − | − | − | − | − | − | ± | + | + |
| Proteus | − | − | − | − | − | − | − | − | − | − | − | − | + | + | + |
| Acinobacter | − | − | − | − | − | − | − | − | − | − | − | − | ± | + | + |
| K. pneumoniae | − | − | − | − | − | − | − | − | ± | + | + | + | + | + | + |
| M. morgani | − | − | − | − | − | − | − | − | − | − | − | − | ± | + | + |
| C. tropicalis | − | − | − | − | − | − | − | − | − | − | − | − | + | + | + |
| C. albicans | − | − | − | − | − | − | − | − | ± | ± | + | + | + | + | + |

TABLE 3

Minimal Inhibitory Concentration in Liquid Medium Ag—Sulfadiazine

| Conc. of Ag+ | 100 ug/mlAg+ Hour | | | 50 ug/ml Hour | | | 40 ug/ml Hour | | | 20 ug/ml Hour | | | 10 ug/ml Hour | | |
| --- | --- | --- | --- | --- | --- | --- | --- | --- | --- | --- | --- | --- | --- | --- | --- |
| Strain | 24 | 48 | 72 | 24 | 48 | 72 | 24 | 48 | 72 | 24 | 48 | 72 | 24 | 48 | 72 |
| E. coli | − | − | − | − | − | − | − | − | − | − | − | − | − | + | + |
| Seratia | − | − | − | − | − | − | − | − | − | − | − | − | ± | + | + |
| Proteus | − | − | − | − | − | − | − | − | − | − | − | − | ± | + | + |
| Acinobacter | − | − | − | − | − | − | − | − | − | − | − | − | + | + | + |
| K. pneumoniae | − | − | − | − | − | − | − | − | − | + | + | + | − | + | + |
| M. morgani | − | − | − | − | − | − | − | − | − | − | − | − | ± | + | + |
| C. tropicalis | − | − | − | − | − | − | − | − | − | − | − | − | − | + | + |
| C. albicans | − | − | − | − | − | − | − | − | − | ± | + | + | + | + | + |

TABLE 4

Minimal Inhibitory Concentration in Liquid Medium AgNO₃ - Control

| Conc. of Ag+ | 100 ug/mlAg+ Hour | | | 50 ug/ml Hour | | | 40 ug/ml Hour | | | 20 ug/ml Hour | | | 10 ug/ml Hour | | |
| --- | --- | --- | --- | --- | --- | --- | --- | --- | --- | --- | --- | --- | --- | --- | --- |
| Strain | 24 | 48 | 72 | 24 | 48 | 72 | 24 | 48 | 72 | 24 | 48 | 72 | 24 | 48 | 72 |
| E. coli | − | − | − | − | − | − | − | − | − | − | − | − | − | + | + |
| Seratia | − | − | − | − | − | − | − | − | − | − | − | − | + | + | + |
| Pseudomonas | − | − | − | − | − | − | − | − | − | − | − | − | ± | + | + |

TABLE 4-continued

Minimal Inhibitory Concentration in Liquid Medium
AgNO₃ - Control

| Conc. of Ag+ | 100 ug/mlAg+ Hour | | | 50 ug/ml Hour | | | 40 ug/ml Hour | | | 20 ug/ml Hour | | | 10 ug/ml Hour | | |
|---|---|---|---|---|---|---|---|---|---|---|---|---|---|---|---|
| Strain | 24 | 48 | 72 | 24 | 48 | 72 | 24 | 48 | 72 | 24 | 48 | 72 | 24 | 48 | 72 |
| Proteus | − | − | − | − | − | − | − | − | − | − | − | − | + | + | + |
| Acinobacter | − | − | − | − | − | − | − | − | − | − | − | − | ± | + | + |
| K. pneumoniae | − | − | − | − | − | − | − | − | − | − | + | + | + | + | + |
| M. morgani | − | − | − | − | − | − | − | − | − | − | − | − | + | + | + |
| C. tropicalis | − | − | − | − | − | − | − | − | − | − | − | − | − | + | + |
| C. albicans | − | − | − | − | − | − | − | − | ± | ± | + | + | + | + | + |

Cultures grown in liquid LB (no NaCl).
With concentrations of Ag ions indicated.

TABLE 5

Efficacy of AgHA and Ag Sulfadiazine as Double Agar Layer
(Thickness of upper layer - 2.0 mm)

| Strain | Ag Hyaluronic Acid (40 μg/ml Ag$^+$) | | | | Ag Sulfadiazine (40 μg/ml Ag$^+$) | | | |
|---|---|---|---|---|---|---|---|---|
| | 24 hour | 48 hour | 73 hour | 96 hour | 24 hour | 48 hour | 72 hour | 96 hour |
| E. Coli | $\frac{0}{1.5 \cdot 10^6} = 0$ | $\frac{0}{1.5 \cdot 10^5} = 0$ | $\frac{0}{1.8 \cdot 10^5} = 0$ | $\frac{0}{1.2 \cdot 10^6} = 0$ | $\frac{0}{1.5 \cdot 10^5} = 0$ | $\frac{0}{1.5 \cdot 10^6} = 0$ | $\frac{0}{1.8 \cdot 10^5} = 0$ | $\frac{0}{1.2 \cdot 10^5} = 0$ |
| Seratia | $\frac{0}{1.4 \cdot 10^4} = 0$ | $\frac{0}{1.9 \cdot 10^5} = 0$ | $\frac{0}{2.0 \cdot 10^5} = 0$ | $\frac{43}{1.0 \cdot 10^5} = 0.043$ | $\frac{0}{1.4 \cdot 10^4} = 0$ | $\frac{0}{1.9 \cdot 10^5} = 0$ | $\frac{0}{2.0 \cdot 10^5} = 0$ | $\frac{0}{1.03 \cdot 10^5} = 0$ |
| Pseudomonas | $\frac{0}{0.6 \cdot 10^4} = 0$ | $\frac{0}{1.8 \cdot 10^4} = 0$ | $\frac{0}{7.3 \cdot 10^4} = 0$ | $\frac{0}{0.5 \cdot 10^4} = 0$ | $\frac{0}{0.6 \cdot 10^4} = 0$ | $\frac{0}{1.8 \cdot 10^4} = 0$ | $\frac{0}{7.3 \cdot 10^4} = 0$ | $\frac{0}{0.5 \cdot 10^4} = 0$ |
| Proteus | $\frac{0}{3.2 \cdot 10^4} = 0$ | $\frac{4}{2.0 \cdot 10^5} = 0.062$ | $\frac{0}{2.2 \cdot 10^5} = 0$ | $\frac{0}{2.0 \cdot 10^5} = 0$ | $\frac{0}{3.2 \cdot 10^4} = 0$ | $\frac{0}{2.0 \cdot 10^5} = 0$ | $\frac{0}{2.2 \cdot 10^5} = 0$ | $\frac{0}{2.0 \cdot 10^5} = 0$ |
| K. Pneumoniae | $\frac{0}{1.1 \cdot 10^4} = 0$ | $\frac{600}{2.3 \cdot 10^5} = 0.3$ | $\frac{0}{1.3 \cdot 10^5} = 0$ | $\frac{0}{7.6 \cdot 10^4} = 0$ | $\frac{0}{1.1 \cdot 10^4} = 0$ | $\frac{0}{2.3 \cdot 10^5} = 0$ | $\frac{0}{1.3 \cdot 10^5} = 0$ | $\frac{0}{7.6 \cdot 10^4} = 0$ |
| Acinobacter | $\frac{0}{2.7 \cdot 10^4} = 0$ | $\frac{1}{2.7 \cdot 10^5} = 0.004$ | $\frac{3}{2.7 \cdot 10^5} = 0.001$ | $\frac{0}{1.0 \cdot 10^5} = 0$ | $\frac{0}{2.7 \cdot 10^4} = 0$ | $\frac{0}{2.7 \cdot 10^5} = 0$ | $\frac{0}{2.7 \cdot 10^5} = 0$ | $\frac{500}{1.0 \cdot 10^5} = 0.5$ |
| C. Albicans | $\frac{90}{10^4} = 0.9$ | $\frac{140}{0.5 \cdot 10^4} = 3$ | $\frac{0}{2.0 \cdot 10^4} = 0$ | $\frac{400}{6.5 \cdot 10^3} = 6$ | $\frac{122}{10^3} = 12.2$ | $\frac{370}{0.5 \cdot 10^4} = 7.4$ | $\frac{160}{2.0 \cdot 10^4} = 0.8$ | $\frac{400}{6.5 \cdot 10^3} = 6$ |
| M. Morgani | $\frac{0}{3.5 \cdot 10^4} = 0$ | $\frac{108}{1.7 \cdot 10^5} = 0.06$ | $\frac{0}{2.2 \cdot 10^5} = 0$ | $\frac{0}{2.5 \cdot 10^5} = 0$ | $\frac{0}{3.5 \cdot 10^4} = 0$ | $\frac{0}{1.7 \cdot 10^5} = 0$ | $\frac{0}{2.2 \cdot 10^5} = 0$ | $\frac{500}{2.5 \cdot 10^5} = 0.2$ |

Results are given in Percent

TABLE 6

Efficacy of AgHA and Ag Sulfadiazine as Double Agar Layer
(Thickness of upper layer - 2.0 mm)

| Strain | Ag Hyaluronic Acid (40 μg/ml Ag⁺) | | | | Ag Sulfadiazine (40 μg/ml Ag⁺) | | | |
|---|---|---|---|---|---|---|---|---|
| | 24 hour | 48 hour | 73 hour | 96 hour | 24 hour | 48 hour | 72 hour | 96 hour |
| *E. Coli* | $\frac{0}{1.5 \cdot 10^6} = 0$ | $\frac{0}{3.0 \cdot 10^5} = 0$ | $\frac{0}{2.6 \cdot 10^4} = 0$ | $\frac{0}{2.3 \cdot 10^4} = 0$ | $\frac{0}{1.5 \cdot 10^6} = 0$ | $\frac{0}{3.0 \cdot 10^4} = 0$ | $\frac{0}{2.6 \cdot 10^4} = 0$ | $\frac{0}{2.3 \cdot 10^4} = 0$ |
| *Seratia* | $\frac{0}{1.4 \cdot 10^4} = 0$ | $\frac{26}{3.0 \cdot 10^5} = 0.2$ | $\frac{160}{2.3 \cdot 10^5} = 0.07$ | $\frac{2000}{1.6 \cdot 10^5} = 1.2$ | $\frac{0}{1.4 \cdot 10^4} = 0$ | $\frac{95}{3.0 \cdot 10^5} = 0.03$ | $\frac{2000}{2.3 \cdot 10^5} = 1$ | $\frac{5000}{1.6 \cdot 10^5} = 3$ |
| *Pseudomonas* | $\frac{60}{0.6 \cdot 10^4} = 1$ | $\frac{253}{1.5 \cdot 10^4} = 1.3$ | $\frac{50}{3.0 \cdot 10^3} = 1.6$ | $\frac{31}{1.0 \cdot 10^3} = 3.1$ | $\frac{0}{0.6 \cdot 10^4} = 0$ | $\frac{576}{1.5 \cdot 10^4} = 4$ | $\frac{260}{3.0 \cdot 10^3} = 9$ | $\frac{600}{1.3 \cdot 10^3} = 46$ |
| *Proteus* | $\frac{0}{3.2 \cdot 10^4} = 0$ | $\frac{1}{10^4} = 0.61$ | $\frac{0}{3.6 \cdot 10^4} = 0$ | $\frac{0}{2.8 \cdot 10^4} = 0$ | $\frac{0}{3.2 \cdot 10^4} = 0$ | $\frac{6}{10^5} = 0.01$ | $\frac{520}{3.6 \cdot 10^4} = 1.4$ | $\frac{800}{2.8 \cdot 10^4} = 3$ |
| *K. Pneumoniae* | $\frac{0}{1.1 \cdot 10^4} = 0$ | $\frac{24}{10^4} = 0.02$ | $\frac{2000}{8.2 \cdot 10^4} = 2.4$ | $\frac{0}{4.0 \cdot 10^4} = 0$ | $\frac{0}{1.1 \cdot 10^4} = 0$ | $\frac{4000}{10^5} = 4$ | $\frac{2000}{8.2 \cdot 10^4} = 2.4$ | $\frac{2000}{2.3 \cdot 10^4} = 8.9$ |
| *Acinobacter* | $\frac{0}{2.7 \cdot 10^4} = 0$ | $\frac{0}{6.5 \cdot 10^4} = 0.01$ | $\frac{32}{3.3 \cdot 10^4} = 0.1$ | $\frac{0}{2.0 \cdot 10^4} = 0$ | $\frac{1}{2.7 \cdot 10^4} = 0.004$ | $\frac{12}{6.5 \cdot 10^3} = 0.2$ | $\frac{2000}{3.3 \cdot 10^4} = 6$ | $\frac{2000}{2.3 \cdot 10^3} = 89$ |
| *C. Albicans* | $\frac{152}{10^3} = 14.2$ | $\frac{600}{1.5 \cdot 10^3} = 40$ | $\frac{300}{1.4 \cdot 10^3} = 21$ | $\frac{560}{2.5 \cdot 10^3} = 22.4$ | $\frac{130}{10^3} = 13$ | $\frac{444}{1.5 \cdot 10^3} = 30$ | $\frac{900}{1.4 \cdot 10^3} = 64$ | $\frac{840}{2.5 \cdot 10^3} = 33$ |
| *M. Morgani* | $\frac{0}{3.5 \cdot 10^4} = 0$ | $\frac{0}{2.4 \cdot 10^5} = 0$ | $\frac{0}{5.2 \cdot 10^4} = 0$ | $\frac{0}{4.6 \cdot 10^4} = 0$ | $\frac{3}{3.5 \cdot 10^4} = 0.01$ | $\frac{600}{2.4 \cdot 10^5} = 0.2$ | $\frac{960}{5.2 \cdot 10^4} = 1.8$ | $\frac{2000}{4.6 \cdot 10^4} = 4$ |

Results are given in Percent

EXAMPLE 5

ANTIMICROBIAL ACTIVITY OF SILVER HYALURONATE

Antimicrobial activity was tested against *Staphylococcus aureus, Escherichia coli, Pseudomonas aeruginosa* and *Candida albicans*.

The tests were performed using two different methods, a Minimum Inhibitory Concentration (MIC) test (1) where the Ag-hyaluronate was added to a liquid growth medium and an Agar Cup Test (2) where the test substance was filled into small wells punched in agar plates.

The results indicates that a concentration of 1% of the Ag-hyaluronate preparation inhibits the growth of the four test strainss. In liquid medium P. aeruginosa was inhibited at a concentration of 0.1%.

The Ag-hyaluronate preparation which was used in the tests contained 16 mg/ml of the silver salt.

Antimicrobial Activity of Ag-hyaluraonate:
Materials and Methods: Ag-hyaluronate.

Test strains: *Escherichia coli* ATCC 8739; *Pseudomonas aeruginosa* ATCC 9027; *Staphylococcus aureus* ATCC 6538; *Candida albicans* ATCC 102 31.

The microorganisms were grown on Trypticase Soy Broth (TSB) at 35°–37° C. for 18–24 hours. Dilutions were made in physiological saline solution.

Test method 1. MIC-test:

Ag-hyaluronate was added to TSB to a final concentration of 1.0%. Solutions with Ag-hyaluronate concentrations of 0.1% and 001% were made by further dilutions in TSB. Test organisms were added to the medium to a concentration of approximately $10^3$ org/ml. The test tubes were then incubated at 35°–37° C. and inspected for visible signs of growth during a period of one week. A turbid medium was recorded as growth. For Candida albicans the presence of a white-colored button at the bottom of the test tube was recorded as growth.

Test method 2. Agar Cup Test:

Overnight cultures of the test strains were diluted in sterile physiological saline. The suspensions were flushed over 14 cm diameter Trypticase Soy Agar plates and excess liquid was removed.

The plates were dried in a laminar air flow unit for 30 minutes. 5 mm diameter wells were punched in the agar. The test solutions were filled in the wells. The plates were incubated at 35°–37° C. and were inspected after overnight incubation. Clear zones surrounding the wells indicated antimicrobial activity. The diameter of the zones were measured.

The following solutions were tested:
Agar Cup Test A:
Ag-hyaluronate (undiluted)
Ag-hyaluronate diluted in distilled water 1:1
Ag-hyaluronate diluted in horse serum (SBL) 1:1
0.01% Thiomersal Reference
Agar Cup Test B:

| | |
|---|---|
| Ag hyaluronate | 1% in TSB |
| Ag hyaluronate | 0.1% in TBS |
| Ag hyaluronate | 0.01% in TBS |
| Ag hyaluronate | 0.001% in TBS |
| Thiomersal | 0.01% in TBS |
| Thiomersal | 0.001% in TBS |

Results are shown in Tables 7, 8 and 9:

TABLE 7

MIC Test

| Test organism | Ag-hyaluronate conc. | | | | |
|---|---|---|---|---|---|
| | 1% | 0.1% | 0.01% | 0.001% | 0% |
| Candida albicans | − | + | + | + | + |
| | − | + | + | + | + |
| E. coli | − | − | + | + | + |
| P. aeruginosa | − | − | + | + | + |
| | − | − | + | + | + |
| S. aureus | − | + | + | + | + |
| | − | + | + | + | + |

+ Growth
− No growth
Duplicate samples

TABLE 8

Agar Cup Test, A
Inhibition zone (mm)

| Test organism | AgHA undiluted | AgHA/ water 1:1 | AgHA/ serum 1:1 | 0.01% Thiomersal |
|---|---|---|---|---|
| S. aureus | 15 | 13 | 12 | 29 |
| C. albicans | 16 | 13 | 15 | 40 |
| P. aeruginosa | 13 | 11 | 11 | 19 |
| E. coli | 14 | 10 | 10 | 17 |

TABLE 9

Agar Cup Test, B
Inhibition zone (mm)

| Test organism | AgHA 1% | AgHA 0.1% | AgHA 0.01% | Thiomersal 0.01% |
|---|---|---|---|---|
| S. aureus | 7 | 5 | 5 | 45 |
| C. albicans | 9 | 5 | 5 | 22 |
| P. aeruginosa | 10 | 5 | 5 | 22 |
| E. coli | 11 | 5 | 5 | 33 |

Discussion:

The results from the MIC-test in liquid medium indicates that a 1% solution of the test substance in Trypticase Soy Broth inhibits the growth of *S. aureus, C. albicans* and *E. coli*. *P. aeruginosa* is inhibited at a concentration of 0.1%. A 1% solution contains 0.16 mg/ml of Ag-hyaluronate.

The tests with agar cup methodology confirms the results from the tests in liquid medium, though the lowest concentration for inhibition of *P. aeruginosa* was 1% Ag-hyaluronate.

When the Ag-hyaluronate was mixed with serum before testing with the agar cup method no significant difference could be measured as compared with Ag-hyaluronate mixed with distilled water.

A white-colored precipitate, probably AgCl, appears immediately when the Ag-hyaluronate comes in contact with culture media or serum.

EXAMPLE 6

PREPARATION OF $^{14}C$ LABELLED HYALURONIC ACID

The biosynthesis of HA by the bacteria involves the utilization of exogenous glucose. The sugar is used mainly as an energy source, while a small portion of it is converted into glucuronic acid and N-acetylglucosamine. These are then incorporated into the HA molecule. Thus, the incorporation of radioactivity can be achieved by feeding carbon-14 labelled glucose into the fermentation broth.

Various experiments were performed, firstly in shake flasks, then in a specially-made pH- and temperature-controlled vessel. It has been found that fermentation in flasks was not efficient resulting both in very low incorporation ratios and low molecular weights. A "minifermentor" has been constructed, with a volume of 5 mL of medium, and studies were performed in this system on the rate of glucose incorporation and utilization. It has been found that at the optimal conditions for HA production, about 5% of the exogeneous glucose is incorporated into HA. The molecular weight of the HA produced in the mini-fermentor was about $2 \times 10^6$ daltons. The system was then used for labelling the HA with $^{14}$C-glucose, and in one fermentation about 20 mg of crude $^{14}$C-HA was obtained. This material was then purified. The yield of this procedure was about 50%, resulting in a final yield of 10 mg of HA of specific activity of 1 uCi of $^{14}$C per mg and a molecular weight of $2.2 \times 10^6$ daltons. The $^{14}$C radioactively labelled NaHA so purified may be converted into radioactively labelled AgHA following the procedures described in Example 1.

EXAMPLE 7

USE OF SILVER HYALURONATE AGAINST *PSEUDOMONAS AERUGINOSA* INFECTION IN A RABBIT EYE MODEL

Introduction

Keratitis produced by *Pseudomonas aeruginosa* is the most rapidly spreading and destructive bacterial disease with which the human cornea can be infected, as well as the most disastrous (Laibson, 1972). The frequency of corneal infections has greatly increased with the use of contact lens. Treatment of early-detected pseudomonas infections with aminoglycosidic antibiotics such as gentamycin usually results in a good therapeutic response. However, the increasing occurrence of antibiotic-resistant bacteria presents a problem, which becomes disastrous when such a situation is detected post-factum. The use of an efficient wide range anti-bacterial agent, such as silver hyaluronate, might overcome this problem.

We used a rabbit model for the demonstration of the efficacy of silver hyaluronate for the treatment of an experimentally-induced pseudomonas keratitis (Hyndiuk, 1981).

Experimental

Bacteria:

A pathogenic hospital isolate of *Pseudomonas aeruginosa* was used. It has been defined by the pseudomonas reference laboratory at the Rambam Medical Center, Haifa, Israel as a polyagglutinin serotype 6. Overnight cultures were grown in tryptic soy broth without dextrose at 37° C. with shaking. In the morning, an aliquot of this culture was diluted 20-fold in fresh broth which was further incubated until a late logarithmic phase was reached (2-3 h.; O.D.$_{660}$-1.2). The concentration of bacteria was estimated from the optical density at 660 nm (1 O.D.=$2 \times 10^9$ cells/ml). The cultures were diluted to the desired density with cold saline. The diluted suspensions were kept at 0°-4° C. until use (1-2 h).

Animal treatment:

New Zealand albino rabbits weighing 2-2.5 kg were used. They were anesthetized by intramuscular injection of ketamine hydrochloride (35 mg/kg) and xylazine hydrochloride (3 mg/kg). A 4 mm circular superficial cut was applied on the cornea with a cork borer, then 3 longitudinal parallel scratches were made inside the circle with a 21 gauge needle. The bacterial infection was inflicted by application of 2 drops (at a 10 min. interval9 of the diluted bacterial suspension.

Preliminary studies were conducted in order to find the optimal concentration of bacteria needed for infection. We found that suspensions of $8 \times 10^7$ bacteria per ml produced 90-100% infection within 30-40 h, whereas a two-fold reduction in bacterial number resulted in lower and variable infection rates. Therefore, all subsequent experiments were performed with suspensions of $8 \times 10^7$ bacteria per ml.

Silver Hyaluronate Treatment:

Initial studies were performed with 0.5% w/v of silver hyaluronate in water prepared as described in Example 1. This solution is quite viscous, but its viscosity does not interfere with the drop-wise application into the eye. However, it was found that at this concentration the treated eyes developed a marked irritation of the conjunctive, irrespective of the bacterial infection. Hence, the 0.5% AgHA solution was diluted three-fold with 0.5% NaHA aqueous solution (final AgHA concentration 0.17%). A slight irritation response was still apparent, but it was transient an disappeared soon after cessation of treatment with the AgHA preparation.

In all experiments, the control eyes were concurrently treated with a 0.5% sodium hyaluronate solution.

Experimental design:

In preliminary experiments, AgHA application was initiated 2, 4 and 8 hours after infection. An anti-bacterial effect of the AgHA therapy was clearly evident with the use of the 4 and 2 h intervals. In the early experiments, hourly application of the AgHA solution was continued for 12 to 24 h only. This scheme resulted in a significant protective effect for 24-48 h after infection, but it did not prevent subsequent advancement of bacterial growth and deterioration of the eyes by 72 h. Therefore, a treatment schedule was selected in which hourly application of one drop of the 0.17% AgHA and 0.33% NaHA solution was used, starting 2 h after infection and continuing for 40 h. Treatment was then continued at 2 h intervals for additional 8-10 h. Two such experiments were performed using 12 or 16 rabbits. In each rabbit, the left eye was treated with the AgHA preparation, while the right eye received 0.5% NaHA and served as a control.

Scoring of the results:

The severity of the infection was scored by: (1) macroscopic examination of the eyes; and (ii) counting of bacteria in isolated cornea.

Visual evaluation was performed according to the following scoring system:

0—No reaction.
1—Leucocyte infiltration associated with the scratches only.
2—Moderate infiltration at the scratches and around them, but not exceeding the 4 mm ring.
3—Infiltration affecting about 30% of the corneal area.
4—Infiltration and turbidity of about 70% of the corneal area and some cellular infiltration into the anterior chamber.
5—Heavy infiltration of the total area of the cornea and anterior chamber as well as development of a central corneal abscess.

The eyes were examined 24, 48 and 72 h after infection. Concurrently, rabbits were sacrificed 48 and 72 h after infection and the cornea were removed and homogenized in saline. The homogenates were then serially diluted and plated on McConkey agar plates for colony counting. Bacteria isolated from the cornea were identified as Pseudomonas aeruginosa by standard biochemical tests and sensitivity to antibiotics.

The scoring results were analyzed statistically by the two tailed Wilcoxon rank sum test.

Results:

AgHA treatment was found to be highly effective in the prevention of Pseudomonas keratitis in the rabbit eye. Table 10 summarizes the results of two experiments performed with a 0.17% AgHA preparation. As shown, the intensive treatment with the silver salt resulted in a marked inhibition of bacterial growth in the treated eyes. The scores of the control eyes were high as early as 42–45 h after infection (scoring index of 3.4–3.6) and increased during the next days to reach a very advanced stage (scoring index of 4.9) by 120 h. In contrast, the mean scores of the treated eyes were significantly lower than those of the control group throughout the experiment (Table 10), and they did not increase beyond 72 h (see Table 10, Experiment I). It should be emphasized that in both experiments, most of the scores of the AgHA treated eyes did not exceed the value of 1. the mean scores shown in Table 10 are somewhat higher than that because in each experiment there were one or two eyes that have escaped AgHA protection.

The effectiveness of the AgHA treatment was also apparent from the fact that no bacteria were found in isolated cornea of treated eyes, whereas an abundant number of pseudomonas microorganisms ($10^5$–$10^6$ bacteria per corneum; Table 10) were found in the control eyes 42–120 h after infection.

Conclusion:

AgHA was shown to have an effective therapeutic effect against the viscous bacteria Pseudomonas aeruginosa, in vivo. The use of such a preparation on its own or in conjunction with the commonly-used antibiotics might prove highly beneficial in the topical treatment of bacterial keratitis.

TABLE 10

Effect of AgHA Treatment of Infected Rabbit Eyes on the Scoring Index and Bacteria Count

| Exp. No. | Time After Infection | Scoring Index (mean + SEM) | | No. of Bacteria/Corneum (Range) | |
|---|---|---|---|---|---|
| | | Control Eye | Treated Eye | Control Eye | Treated Eye |
| I | 45 h | 3.62 ± 1.11 (N = 12) | 1.44 ± 0.97*** (N = 12) | (a) | (a) |
| | 72 h | 4.29 ± 1.50 (N = 7) | 1.79 ± 1.55* (N = 7) | (b) | (b) |
| | 120 h | 4.86 ± 0.87 (N = 16) | 1.86 ± 1.55** (N = 16) | $1.5 \times 10^5 = 2.4 \times 10^6$ (N = 4) | $<10^3$ (N = 3) |
| II | 42 h | 3.41 ± 1.70 (N = 16) | 0.84 ± 0.65*** (N = 16) | $5 \times 10^5 - 4 \times 10^6$ (N = 4) | $<10^3$ (N = 5) |
| | 66 h | 4.22 ± 1.64 (N = 9) | 1.50 ± 1.20** (N = 9) | $3 \times 10^4 - 5 \times 10^6$ (N = 6) | $<10^3$ (N = 6) |

*p 0.05: control vs. treated
**p 0.01
***p 0.001
(a) samples lost
(b) note determined

REFERENCES

1. Carr, H. S., T. J. Wlodkowski and H. S. Rozenkrantz, "Silver Sulfadiazine: In Vitro Antibacterial Activity", Antimicrob. Agents and Chemoterhapy 4: 585–587 (1973).
2. Dettch, E. A., A. A. Marino, T. E. Gillespie and J. A. Albright, "Silver-nylon: A New Antimicrobial Agent", Antimicrob. Agents and Chemotherapy 23: 356–359 (1982).
3. Roseman, S. et al, "Biosynthesis of Hyaluronic Acid By Group A Streptococcus", Biol. Chem. 203, 212–225 (1953).
4. Hyndiuk, R. A., "Experimental Pseudomonas Keratitis", Tr. Am. Ophth. Soc. 79: 541–624 (1981).
5. Laibson, P. R., "Cornea and Sclera", Opthamol 88: 553–574 (1972).

What is claimed is:

1. A method of treating a subject having keratitis which method comprises topically applying to an infection causing the keratitis an effective amount of a silver salt of hyaluronic acid.

2. A method of claim 1, wherein an antibiotic is used in conjunction with the silver salt of hyaluronic acid.

* * * * *